(12) United States Patent
Yi

(10) Patent No.: US 12,257,135 B1
(45) Date of Patent: Mar. 25, 2025

(54) SMART DEFECATION DETECTION DEVICE AND HEALTHCARE SYSTEM INCLUDING THE SAME

(71) Applicant: LEETEK LIFE CO., LTD, Bucheon-si (KR)

(72) Inventor: Won Jang Yi, Goyang-si (KR)

(73) Assignee: LEETEK LIFE CO., LTD, Bucheon-si (KR)

( * ) Notice: Subject to any disclaimer, the term of this patent is extended or adjusted under 35 U.S.C. 154(b) by 0 days.

(21) Appl. No.: 18/794,065

(22) Filed: Aug. 5, 2024

Related U.S. Application Data

(63) Continuation of application No. PCT/KR2024/007181, filed on May 27, 2024.

(30) Foreign Application Priority Data

Dec. 7, 2023 (KR) .................. 10-2023-0176348

(51) Int. Cl.
*A61F 13/42* (2006.01)
*A61F 13/84* (2006.01)
*H04L 67/12* (2022.01)

(52) U.S. Cl.
CPC ........ *A61F 13/42* (2013.01); *A61F 2013/424* (2013.01); *A61F 2013/8482* (2013.01); *H04L 67/12* (2013.01)

(58) Field of Classification Search
CPC .............. A61F 13/42; A61F 2013/424; A61F 2013/8482; A61F 13/00; A61F 13/15;
(Continued)

(56) References Cited

U.S. PATENT DOCUMENTS

2021/0071401 A1* 3/2021 Shen .................. G06F 18/214
2022/0074918 A1* 3/2022 Hall .................... G01N 33/4833

FOREIGN PATENT DOCUMENTS

JP 0362292 U 6/1991
JP 08164167 A 6/1996
(Continued)

OTHER PUBLICATIONS

International Search Report of PCT/KR2024/007181 dated Sep. 4, 2024.
(Continued)

*Primary Examiner* — James J Yang
*Assistant Examiner* — Anthony D Afrifa-Kyei
(74) *Attorney, Agent, or Firm* — Jae Youn Kim; NKL Law

(57) ABSTRACT

Provided is a healthcare system including a smart defecation detection device. The healthcare system according to an embodiment of the present invention includes: a smart defecation detection device that is detachable to a wearable object of a protected person and detects defecation of the protected person, wherein the smart defecation detection device is provided as one of a plurality of smart defecation detection devices; a relay device that receives detection information in real time from the plurality of smart defecation detection devices; a control server that receives the detection information of the plurality of smart defecation detection devices in real time from the relay device, and comprehensively manages whether a defecation event has occurred and whether processing of the defecation event has been completed for each protected person, based on the detection information; and a reception device configured to receive notification information so that an assigned manager or ward/management station in charge of the protected person in whom the defecation event has occurred is allowed
(Continued)

to be aware of the defecation event when it is determined that the defecation event has occurred based on the detection information of the smart defecation detection device.

6 Claims, 9 Drawing Sheets

(58) Field of Classification Search
CPC .......... A61F 2013/421; A61F 2013/422; A61F 2013/423; A61F 2013/425; A61F 2013/426; A61F 2013/427; A61F 2013/428; A61F 2013/429; H04L 67/12; G06Q 50/26; G07C 9/32; G07C 9/00; G07C 9/30; G07C 9/33; G07C 9/35; G07C 9/37; G07C 9/38; G08B 21/02; A61B 5/6808; G01N 27/223
See application file for complete search history.

(56) References Cited

FOREIGN PATENT DOCUMENTS

| | | | |
|---|---|---|---|
| JP | 09131382 | A | 5/1997 |
| JP | 2020131491 | A | 8/2020 |
| KR | 1020160050354 | B1 * | 5/2016 |
| KR | 101656510 | B1 | 9/2016 |
| KR | 10-1925285 | B1 | 12/2018 |
| KR | 102042627 | B1 | 11/2019 |
| KR | 102116665 | B1 | 5/2020 |
| KR | 1020200095224 | A * | 8/2020 |
| KR | 10-2184237 | B1 | 11/2020 |

OTHER PUBLICATIONS

Written Opinion of the International Searching Authority of PCT/KR2024/007181 dated Sep. 4, 2024.

* cited by examiner

SMART DEFECATION DETECTION DEVICE AND HEALTHCARE SYSTEM INCLUDING THE SAME

TECHNICAL FIELD

Embodiments of the present invention relate to a smart defecation detection device and a healthcare system including the same.

BACKGROUND ART

Generally, patients with limited mobility, elderly people, children with certain disabilities, infants, etc. always need someone's help to defecate. However, since it is difficult for guardians to always check for defecation and provide assistance 24 hours a day, disposable diapers are worn whenever possible.

However, even in the case in which a diaper is used to defecate, when the diaper cannot be changed at an appropriate time, secondary diseases, such as skin rashes caused by wet diapers, urinary tract infections caused by bacteria in feces, such as *Escherichia coli*, dysentery, *Staphylococcus aureus*, and the like, etc., may occur. Further, in nursing homes, hospitals, etc. where many elderly people/patients live together, elderly people/patients in hospital rooms suffer from an unsanitary environment due to defecation being left unattended due to diapers not being changed.

In this case, the elderly or patients who are left wearing diapers not only experience continued discomfort, but are also forced to feel mental stress, such as feeling ashamed of the elderly or patients in the same hospital room.

In order to solve the above problem, a guardian or a manager should continuously monitor defecation, but it is not only realistically difficult to continuously visit the protected person (patient or elderly people, etc.) to check, but it is also not easy to check defecation. There is also a problem in that the work burden is very large for a small number of managers to continuously manage defecation states of a plurality of the protected persons, and systematic management is difficult because monitoring and post-processing should be left to individual capabilities.

In order to solve the above problem, in the related art, a technology for wirelessly receiving a defecation/urination detection signal by attaching a tag for disposable defecation/urination detection with a unique ID to a diaper, coming the tag into contact with a radio frequency identification (RFID) reader when the tag is attached to the diaper, and registering the tag in the RFID reader is disclosed. However, in the related art, since the tag for defecation/urination detection should be registered with the RFID reader every time a diaper is replaced, a problem occurs in that the workload of managers who should manage a plurality of protected persons is increased.

In addition, in the related art, since the tag for defecation/urination detection should be attached to an inner side of the diaper, there is a problem in that the tag is difficult to reuse.

DISCLOSURE

Technical Problem

Embodiments of the present invention are directed to providing a technology for monitoring in real time whether a defecation event occurs for each protected person without a visit from a manager, in an environment where a plurality of protected persons are managed by each manager.

Embodiments of the present invention are also directed to providing a technology for transmitting a notification to a manager in charge of managing a protected person when a defecation event occurs for each protected person, so that the manager in charge can rapidly check the fact that the defecation event has occurred and information on the protected person in whom the defecation event has occurred.

Embodiments of the present invention are also directed to providing a technology for preventing a protected person from being left unattended by checking a current state of defecation event processing in real time when a defecation event occurs for each protected person.

Embodiments of the present invention are also directed to providing a technology for not only comprehensively managing real-time detection information, defecation event occurrence information, and defecation event processing information of each smart defecation detection device at a ward/management station, but also analyzing a current defecation state and defecation-related habit information for each protected person through the corresponding information and predicting a defecation pattern.

Embodiments of the present invention are also directed to providing a technology for facilitating customized management for each protected person by a manager by analyzing an optimal bathing cycle or an optimal bathing time for each protected person based on the analyzed current defecation state and defecation-related habit information, and information on the predicted defecation pattern for each protected person.

Technical Solution

A healthcare system including the smart defecation detection device according to an embodiment of the present invention, which includes: a smart defecation detection device that is detachable to a wearable object of a protected person and detects defecation of the protected person, wherein the smart defecation detection device is provided as one of a plurality of smart defecation detection devices; a relay device that receives detection information in real time from the plurality of smart defecation detection devices; a control server that receives the detection information of the plurality of smart defecation detection devices in real time from the relay device, and comprehensively manages whether a defecation event has occurred and whether processing of the defecation event has been completed for each protected person, based on the detection information; and a reception device configured to receive notification information so that an assigned manager or ward/management station in charge of the protected person in whom the defecation event has occurred is allowed to be aware of the defecation event when it is determined that the defecation event has occurred based on the detection information of the smart defecation detection device, wherein information on the protected person matching each smart defecation detection device and information on the assigned manager in charge of the protected person are registered in the control server, the notification information includes information on the protected person in whom the defecation event has occurred and information on a time of occurrence of the defecation event, and when defecation event processing by the assigned manager is completed, a defecation event processing completion signal is received by the control server.

Further, the smart defecation detection device may include: a battery unit provided to be rechargeable; a wireless communication unit provided to wirelessly communicate with the relay device; and a detection unit that detects an electrical signal according to the defecation state of the wearable object, and the electrical signal of the detection unit may be changed based on detecting of at least one of ammonia, humidity, and temperature is changed.

Further, the smart defecation detection device may be re-attached after the assigned manager replaces the wearable object in which the defecation event has occurred with a new wearable object.

Further, the information on the assigned manager may include manager code information, the control server may match the assigned manager in charge of the smart defecation detection device to a manager working in real time, based on commuting information of the manager and the manager code information matching each manager each time he or she gets to work, and the notification information may be transmitted to a manager terminal of the matched manager working in real time based on the manager code information matched to the smart defecation detection device where the defecation event has occurred.

Further, the control server may receive the detection information of each of the smart defecation detection devices in real time, process to monitor a defecation event occurring in the smart defecation detection device and a defecation processing status, and collect and analyze information obtained from the monitoring, and the control server may predict a defecation pattern for each protected person based on the collected and analyzed information and recommend an optimal bathing cycle or an optimal bathing time for each protected person based on the predicted defecation pattern for each protected person.

Further, the control server may receive the detection information of each of the smart defecation detection devices in real time, process to monitor a defecation event occurring in the smart defecation detection device and a defecation processing status, and analyze a current defecation state and defecation-related habit information for each protected person based on information obtained from the monitoring, the defecation-related habit information may include bedsore history of the protected person, skin sensitivity information, and information on the level of psychological sensitivity of the protected person, the information on the time of the occurrence of the defecation event may include information on a remaining time from a time point of the occurrence of the defecation event to a processing request time, and the control server may recommend and set a customized processing request time when the defecation event occurs for each protected person, based on the defecation-related habit information for each protected person.

Further, the assigned manager may include a primary manager and a deputy manager, and when the defecation event processing completion signal is not received by the control server within a set time from a time point at which the notification information is transmitted to the reception device, the notification information may be transmitted to a manager terminal of the deputy manager.

Advantageous Effects

In an environment where a plurality of protected persons are managed by each manager, it is possible to monitor a defecation event for each protected person in real time, and it is possible to prevent the occurrence of secondary diseases in the protected person due to neglect of the defecation event and increase the self-esteem of the protected person by systematically managing processing status of the defecation event.

In an environment where a plurality of protected persons are managed by each manager, by receiving notification of the occurrence of a defecation event through a smart defecation detection device of a diaper worn by each protected person, unnecessary work of continuously visiting each protected person to check whether a defecation event occurs for each protected person can be omitted.

Further, it is possible to analyze the defecation characteristics of each protected person and predict a defecation cycle, and it is possible to analyze an optimal bathing cycle or an optimal bathing time for each protected person based on a defecation pattern of the protected person.

Further, in facilities such as nursing homes and hospitals that manage a plurality of protected persons, managers can be efficiently managed and the number of indiscriminate diaper changes can be reduced, thereby reducing diaper usage.

Further, a smart defecation detection device matched to each protected person is not only reusable continuously through detachment or attachment, but can also be reused through new matching to a new protected person, and thus it is possible to reduce the cost of defecation detection.

In addition, based on defecation analysis information for each protected person using the smart defecation detection device, consultation with the protected person and a guardian of the protected person can be facilitated and trust with them can be secured.

MODES OF THE INVENTION

Figure 1:
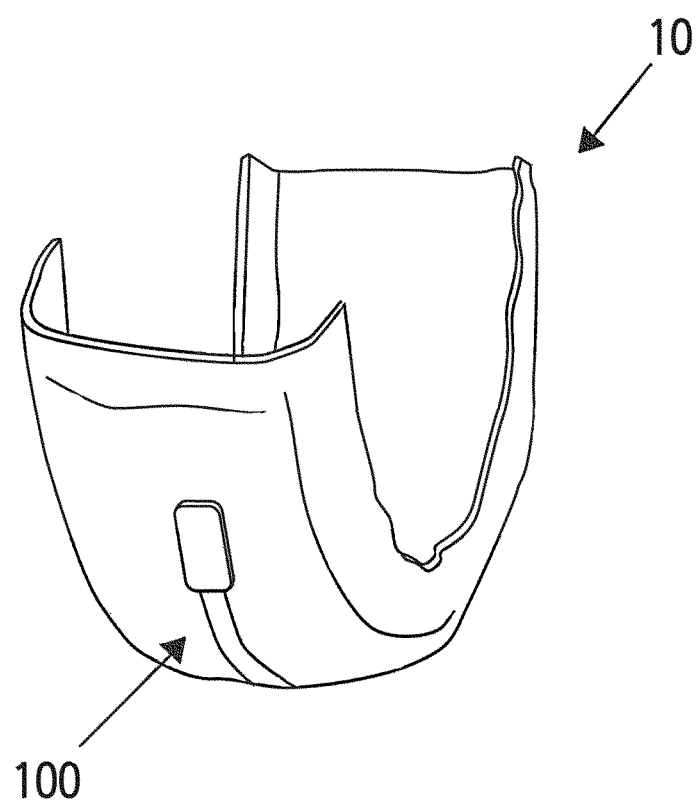
FIG. 1 is a diagram illustrating a smart defecation detection device attached to a diaper according to an embodiment of the present invention.

Hereinafter, embodiments of the present invention will be described in detail with reference to the accompanying drawings. However, the embodiments of the present invention may be modified in various ways and the scope of the patent application is not restricted or limited by these embodiments. It should be understood that all modifications, equivalents, or alternatives for the embodiments are included in the scope of the present invention.

Specific structural or functional descriptions of the embodiments are disclosed for illustrative purposes only and may be modified and implemented in various forms. Therefore, the embodiments are not limited to the specific disclosed form, and the scope of this specification includes modifications, equivalents, or alternatives included in the technical spirit.

It should be understood that, although the terms "first," "second," and the like may be used herein to describe various elements, the terms should be only used to distinguish one element from another element. For example, a first element could be termed a second element, and, similarly, a second element could be termed a first element.

It should be understood that when an element is referred to as being "connected" or "coupled" to another element, the element may be directly connected or coupled to another element or intervening elements may be present.

The terminology used herein is for the purpose of describing particular embodiments only and is not intended to be limiting to the present invention. As used herein, the singular forms "a" and "an" are intended to also include the plural forms, unless the context clearly indicates otherwise. It should be further understood that the terms "comprise," "comprising," "include," and/or "including" when used herein, specify the presence of stated features, integers, steps, operations, elements, parts, or combinations thereof, but do not preclude the presence or addition of one or more other features, integers, steps, operations, elements, parts, or combinations thereof.

Unless otherwise defined, all terms including technical and scientific terms used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Further, in describing of the embodiments with reference to the accompanying drawings, the same elements are denoted by the same reference numerals regardless of reference numbers, and thus the description thereof will not be repeated. In describing of the embodiments of the present invention, when it is determined that detailed descriptions of related well-known technologies unnecessarily obscure the gist of the embodiments of the present invention, the detailed descriptions thereof will be omitted.

Advantages and features of the present invention and methods of achieving the same will be clearly understood with reference to the accompanying drawings and embodiments described in detail below. However, the present invention is not limited to the embodiments to be disclosed below but may be implemented in various different forms. The embodiments are provided in order to fully explain the present embodiments and fully explain the scope of the present invention for those skilled in the art. The scope of the present invention is only defined by the appended claims.

In the embodiments of the present invention, unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The shapes, sizes, proportions, angles, numbers, etc. disclosed in the drawings for explaining the embodiments of the present invention are illustrative, and the present invention is not limited to the matters illustrated. Further, in descriptions of the present invention, when detailed descriptions of related known technologies are deemed to unnecessarily obscure the gist of the present invention, the detailed descriptions will be omitted. When the terms "include," "have," "consist of," etc. described in this specification are used, other parts may be added unless the term "only" is used. An element referred to in the singular encompasses the expression in the plural unless specifically stated otherwise.

In interpreting elements, it should be interpreted to include the margin of error even when there is no separate explicit description.

In describing of a positional relationship, for example, in the case where a positional relationship between two portions is described as with the terms "on ~," "on the top of ~," "on the bottom of ~," "next to ~," or the like, one or more portions may be interposed therebetween unless the term "directly" is used in the expression.

When a first element or layer is referred to as "on" a second element or layer, it includes both of the case where the first element or layer is directly disposed on the second element or layer and the case where a third element or layer is interposed therebetween. Like reference numerals refer to like elements throughout the specification.

Since sizes and thicknesses of elements in the drawings are arbitrarily illustrated for convenience of description, the following embodiments are not limited thereto.

Each feature of the various embodiments of the present invention may be partially or fully combined or combined with each other, and as can be fully understood by those skilled in the art, various technical interconnections and operations are possible, and the respective embodiments may be implemented independently of each other or may be conducted together with each other due to a related relationship.

Figure 2:
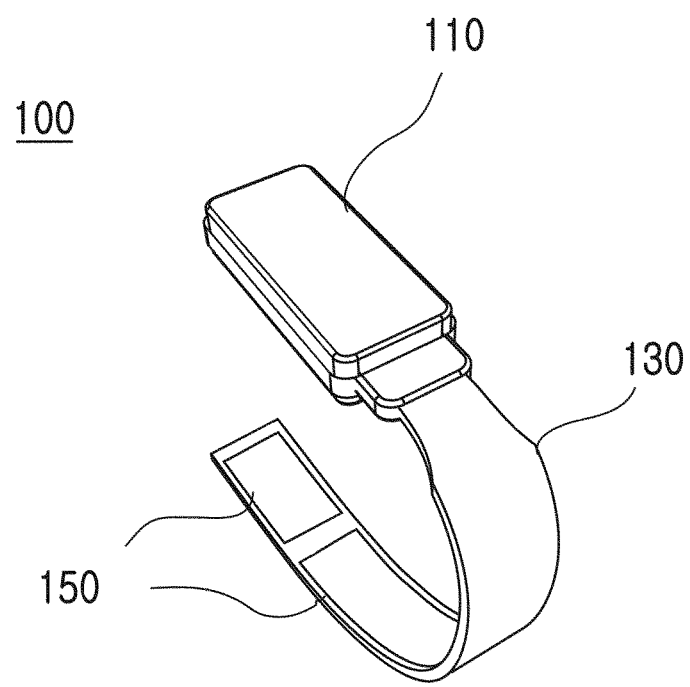
FIG. 2 is a perspective view of the smart defecation detection device.

FIG. 1 is a diagram illustrating a smart defecation detection device attached to a diaper according to an embodiment of the present invention. FIG. 2 is a perspective view of the smart defecation detection device.

Referring to FIGS. 1 and 2, a smart defecation detection device 100 according to the embodiment of the present invention may be attached to a wearable object 10 and detect defecation of a protected person.

The wearable object 10 may be a diaper or underwear worn by the protected person to resolve the defecation of the protected person. Specifically, the wearable object 10 may be a disposable diaper.

In the present invention, the protected person is a person who needs protection to resolve defecation, such as the elderly with impaired mobility, seriously ill patients, disabled children, infants, etc.

The smart defecation detection device 100 may include a detection unit 130 that detects the defecation of the protected person, a processing unit 110 that processes an electrical signal detected by the detection unit 130, and an attachment portion 150 for being attached or detached to the wearable object 10.

For example, the detection unit 130 may be provided in the form of a band. Specifically, the detection unit 130 may be formed in the form of a band extending in a front-back direction to correspond to a defecation area of the wearable object 10.

The detection unit 130 may be configured to detect a defecation state of the wearable object 10, and specifically, may detect an electrical signal according to the defecation state.

The detection unit 130 may include an electrode layer that detects the electrical signal, a shield layer for blocking a signal detected by an external environment rather than the defecation state of the wearable object 10, and a protective layer for protecting the electrode layer and the shield layer.

Further, the detection unit 130 may detect a defecation event using the fact that an electrical characteristic value changes when the defecation event occurs in the wearable object 10. In this case, the electrical characteristic value may be electrostatic capacity.

For example, the detection unit 130 may use an electrical characteristic value that changes due to ammonia when ammonia is generated.

As another example, the detection unit 130 may use an electrical characteristic value that changes depending on the humidity when the humidity changes.

As still another example, the detection unit 130 may use an electrical characteristic value that changes depending on the temperature when the temperature changes.

The electrical characteristic value detected by the detection unit 130 may change depending on the defecation state of the wearable object 10, and the electrical signal according to the change in electrical characteristic values may be transmitted to the processing unit 110.

The processing unit 110 may be configured to process the signal detected by the detection unit 130. Specifically, the processing unit 110 may receive and analyze the signal detected by the detection unit 130, determine information on the presence of urine, the presence of feces, and the amount of feces, and transmit detection information to the relay device 200.

For example, the detection information may include at least one piece of information of a value of the detected signal, the presence of urine, the presence of feces, the amount of feces, and the remaining battery percentage.

Further, the attachment portion 150 may be located on one surface of the detection unit 130 or the processing unit 110, and may be configured as a portion for attaching or detaching the wearable object 10.

The attachment portion 150 may be provided in a longitudinal direction of the detection unit 130, which is provided in the form of a band.

The attachment portion 150 may be configured so that its attachment force does not decrease even when the number of attachments or detachments increases. For example, the attachment portion 150 may be a Velcro device.

The smart defecation detection device 100 may be attached to be located on an outer surface of the wearable object 10. That is, since the smart defecation detection device 100 is not brought into direct contact with the skin of the protected person, it is possible to prevent secondary infection, discomfort, or the like in the protected person even when the smart defecation detection device 100 is reused.

Further, when the wearable object 10 is replaced due to the occurrence of the defecation event of the protected person, it is possible to prevent the defecation from being brought into contact with the smart defecation detection device 100, and thus the cleanliness of the smart defecation detection device 100 may be maintained. In addition, the work burden of a manager in charge of the protected person may be reduced because there is no need to clean the smart defecation detection device 100.

As another example, the smart defecation detection device 100 may further include a waterproof cap (not illustrated) that covers an exterior of the smart defecation detection device 100. Even when the smart defecation detection device is contaminated due to leakage of the defecation caused by the protected person's tossing and turning or contamination of the outside of the diaper, the smart defecation detection device may be washed with water using the waterproof cap.

Figure 3:
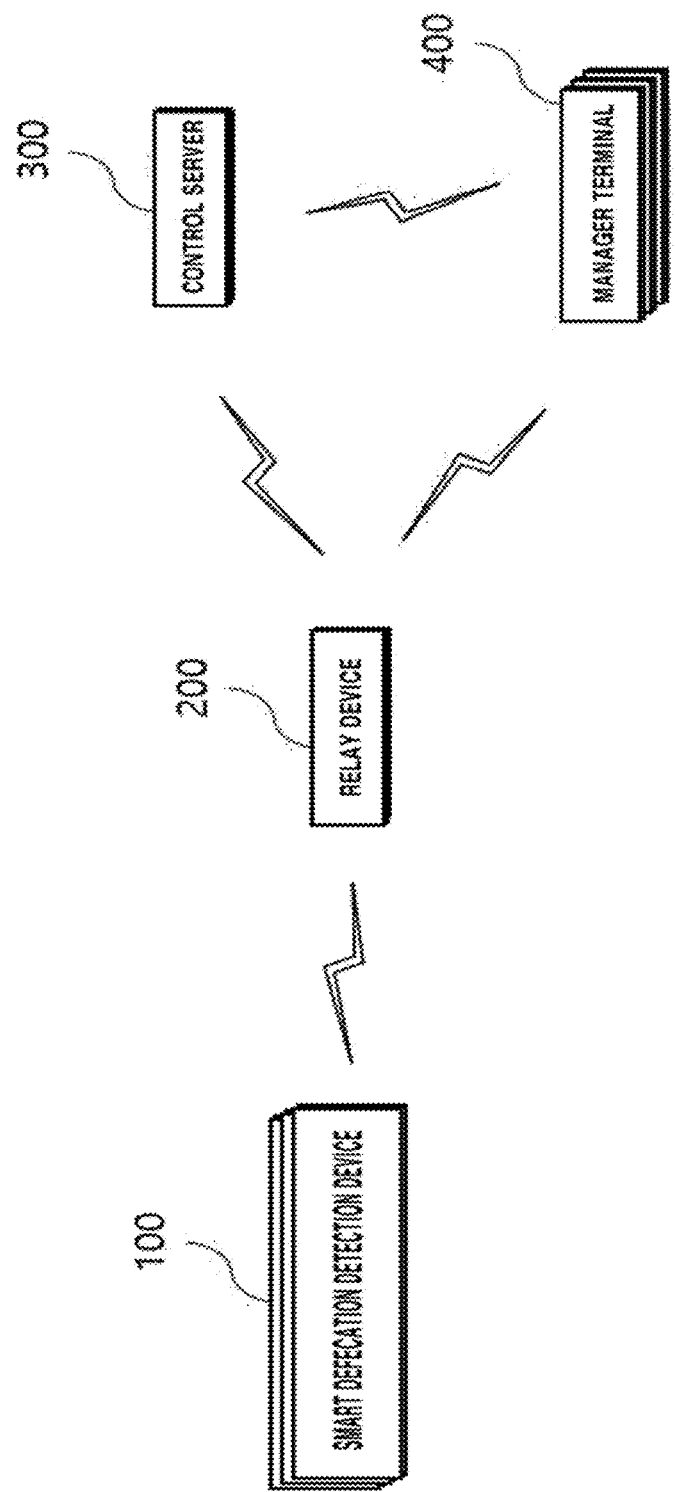
FIG. 3 is a block diagram illustrating a configuration of a healthcare system including the smart defecation detection device.

FIG. 3 is a block diagram illustrating a configuration of a healthcare system including the smart defecation detection device.

Referring to FIG. 3, a healthcare system 1 including the smart defecation detection device 100 of the present invention may detect defecation in each of a plurality of smart defecation detection devices 100 respectively attached to wearable objects of different protected persons, transmit information on the detection to a relay device 200 through a communication network, transmit the information on the detection and a notification from the relay device 200 to a control server 300 and/or a manager terminal 400 through a communication network, and collect, analyze, and monitor in real time information on states of defecation of a plurality of protected persons and whether the defecation is processed.

Accordingly, the healthcare system 1 not only may rapidly check the occurrence of a defecation event of a protected person occurring in each smart defecation detection device 100 and enable the manager to respond rapidly, but also predict health analysis and a defecation pattern by analyzing a current defecation state of each protected person.

Further, through the healthcare system 1, it becomes easy for a single manager to manage the plurality of protected persons, and it is possible to systematically manage defecation events of protected persons and real-time event processing.

The healthcare system 1 of the present invention may include a smart defecation detection device 100, a relay device 200, a control server 300, and a manager terminal 400.

The smart defecation detection device 100 may be communicatively connected to the relay device 200 through a first communication network, and the control server 300 may be communicatively connected to the relay device 200 through a second communication network. The manager terminal 400 may be communicatively connected to the relay device 200 through a third communication network. Further, the control server 300 may be communicatively connected to the manager terminal 400 through a fourth communication network.

The first to fourth communication networks include wired and wireless communication networks, mobile communication networks, etc., and may each be provided as a single communication network for each of them or may be provided as a complex communication network combining them.

Specifically, the first to fourth communication networks may be, for example, any one of radio frequency (RF) communication, Bluetooth, Zigbee communication, Wi-Fi, and long range (LoRa) communication.

Preferably, the first communication network may be any one of RF communication and Bluetooth, the second communication network may be any one of Wi-Fi and data communication, and the third and fourth communication networks may be any one of RF communication, Wi-Fi, and data communication.

The smart defecation detection device 100 may be connected to the relay device 200 through the first communication network. The smart defecation detection device 100 may transmit detection information detected by the detection unit 130 to the relay device 200 through the first communication network in real time.

The relay device 200 may be connected to each of the plurality of smart defecation detection devices 100 through the first communication network, and receive the detection information from each of the smart defecation detection devices 100.

The relay device 200 may be connected to the control server 300 through the second communication network, and include identification information (protected person information, manager information, Internet Protocol (IP) address, etc.) of the smart defecation detection device 100 and the relay device 200 so that the identification information can be identified by the control server 300. The relay device 200 may transmit the detection information of each of the smart defecation detection devices 100 to the control server 300 in real time.

The control server 300 may be provided for comprehensively management of the plurality of smart defecation detection devices 100, for example, in a control center, central ward station, etc., and register and manage information on each of the plurality of smart defecation detection devices 100 and information on the relay device 200.

For example, ID information of each smart defecation detection device 100, information on the protected person corresponding to each smart defecation detection device 100, and information on the manager may be registered.

For example, the information on the protected person may be location information of the protected person or name information of the protected person. For example, the location information of the protected person may be a hospital room or a bed number.

As another example, the location information of the protected person may be a classroom, a seat number, or a GPS location.

For example, the manager information may be information (name, ID, etc.) of the manager in charge of each protected person. In this case, the manager in charge may include information on a primary manager in charge mainly and information on a deputy manager in charge secondarily.

As another example, the manager information may be manager code information. Specifically, since a plurality of managers often work in shifts in nursing homes, hospitals, etc., the manager in charge of each protected person may change depending on a time zone. In consideration of the above, the manager information matching each smart defecation detection device 100 may be registered as the manager code information, and each manager may match the manager code information corresponding to the manager during working hours whenever the manager goes to work, so that it is possible to prevent the absence of the manager in charge of each protected person at any time.

Further, when a defecation event occurs for each protected person, a notification may be transmitted only to the manager who is at work.

Further, the managers may be divided into a primary manager and a deputy manager, and each manager may match both primary manager code and deputy manager code when getting to work. For example, a single manager may be matched to primary manager code 03 and deputy manager code 04. That is, the single manager may manage a defecation event of a protected person wearing the wearable object 10 to which the smart defecation detection device 100 corresponding to the primary manager code 03 is attached, and at the same time, may additionally manage a defecation event of a protected person wearing the wearable object 10 to which the smart defecation detection device 100 corresponding to the deputy manager code 04 is attached.

Therefore, when a defecation event occurs for a specific protected person, the deputy manager may respond in a complementary manner even when the primary manager cannot immediately respond to the event, so that the defecation event can always be processed rapidly.

The control server 300 may recognize the identification information of each of the smart defecation detection devices 100 through the detection information transmitted from the relay device 200, and monitor a state of the smart defecation detection device 100 in real time (whether a defecation event has occurred, remaining battery percentage, whether defecation event processing is completed, etc.).

The control server 300 may register and manage the plurality of smart defecation detection devices 100 and the information on the managers in charge of management of the protected persons corresponding to the plurality of smart defecation detection devices 100. The control server 300 may transmit the detection information on the smart defecation detection device 100 to the manager terminal 400 of the manager in charge in real time so that the manager in charge of each smart defecation detection device 100 monitors the state of the smart defecation detection device 100 in real time.

As another example, the relay device 200 may transmit the detection information on each smart defecation detection device 100 to the manager terminal 400 of the manager in charge through the fourth communication network in real time.

The control server 300 may collect, store, and manage the detection information of each of the plurality of smart defecation detection devices 100 through the relay device 200. For example, the control server 300 may analyze the collected detection information through a pre-stored program or artificial intelligence-based machine learning technology to analyze a current defecation state and defecation-related habit information for each protected person.

For example, the current defecation state may be the number of times of defecation, a defecation cycle, a defecation state, etc. The defecation-related habit information may be bedsore history for each protected person, information on skin sensitivity, information on the level of psychological sensitivity of the protected person, etc.

For example, the control server 300 may analyze a health condition for each protected person and predict a defecation pattern based on the analyzed information.

For example, the control server 300 may analyze and recommend an optimal bathing cycle and/or an optimal bathing time for each protected person based on the current defecation state, the defecation-related habit information, and the defecation pattern for each protected person. Using the optimal bathing cycle and/or optimal bathing time for each protected person, the manager may systematically manage a bathing schedule of each protected person, thereby dispersing work concentration and reducing workload.

Further, the control server 300 may recommend and set a customized processing request time when a defecation event occurs for each protected person, based on the defecation-related habit information for each protected person.

The control server 300 may perform data-processing on the detection information and the analysis information by protected person, day/month/year, event occurrence status, notification occurrence status, administrator processing status, etc. and make the data as a list, and store and manage the processed and listed data. Further, the control server 300 may build big data using the data, process the big data through machine learning, manage the information and notification details of protected persons in which events frequently occur, predict whether an event occurs and the possibility of event occurrence for each time slot, and further predict the minimum number of managers required for each specific time slot.

Accordingly, nursing homes, hospitals, etc. may not only efficiently manage their managerial staff and prevent unnecessary waste of costs, but also provide high-quality services to their protected persons and guardians.

When a defecation event occurs or a defecation event is predicted during real-time monitoring, the control server 300 may output notification information to a monitoring device 380 of the control server 300 or the manager terminal 400, which will be described below. In this case, when the defecation event occurs or the defecation event is predicted, the notification information indicating the occurrence of the defecation event may be transmitted to the manager terminal 400 of the manager in charge of the smart defecation detection device 100. In this case, the notification information may include information on the smart defecation detection device 100 where the defecation event has occurred or is likely to occur, protected person information, detection information, defecation event occurrence history, etc.

As another example, the manager terminal 400 may directly receive the detection information and the notification information of the smart defecation detection device 100 from the relay device 200.

Further, the control server 300 may determine whether to output the notification information through the monitoring device 380 or the manager terminal 400.

Figure 4:
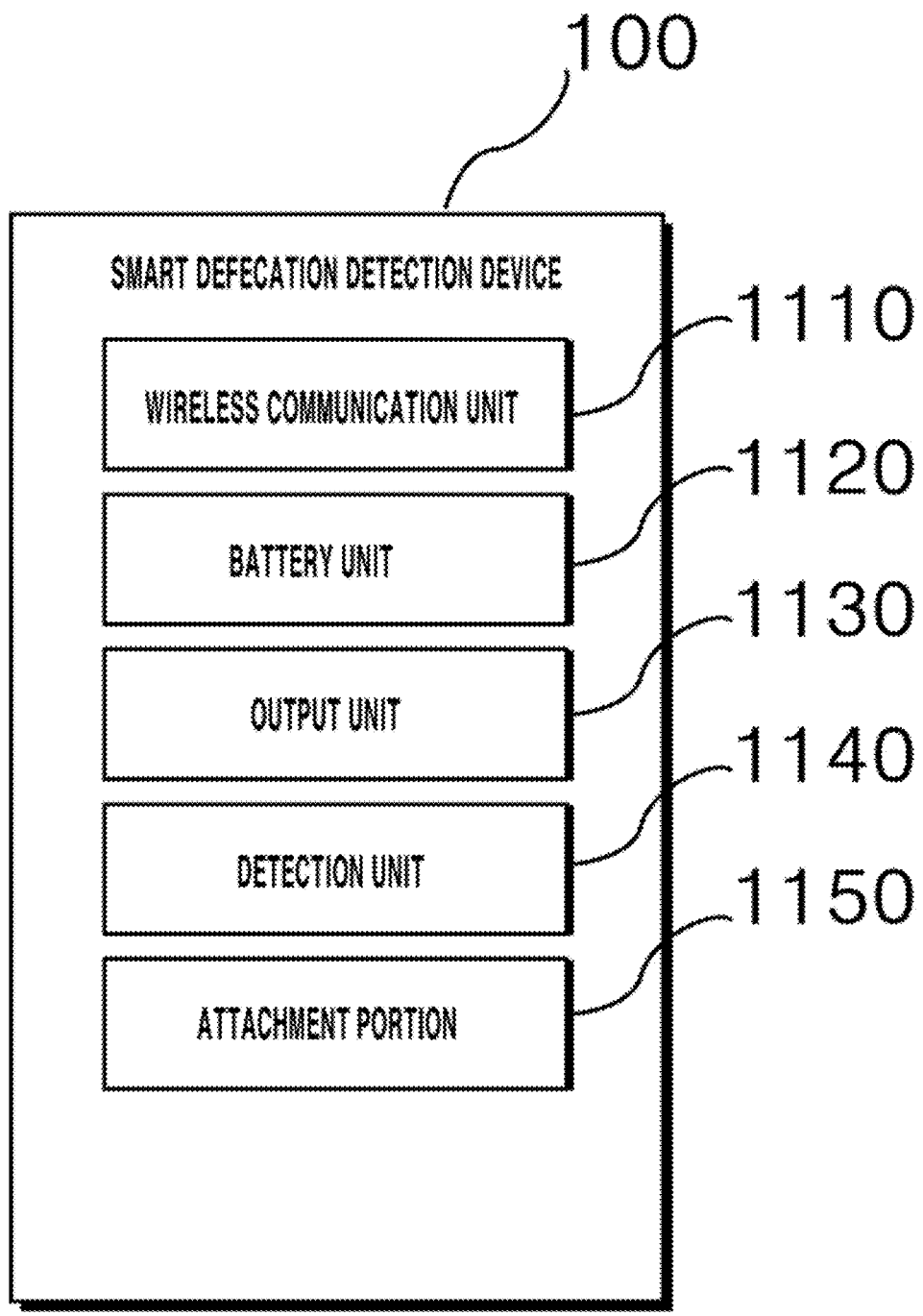
FIG. 4 is a block diagram illustrating a configuration of the smart defecation detection device.

FIG. 4 is a block diagram illustrating a configuration of the smart defecation detection device.

Referring to FIG. 4, the smart defecation detection device 100 may include a detection unit 130, a processing unit 110, and an attachment portion 150.

The processing unit 110 may include a wireless communication unit 1110 that transmits a detection signal detected by the detection unit 130 to a relay device 200, which will be described later, and a battery unit 1120 for supplying power. The battery unit 1120 may be of a charging type.

For example, the wireless communication unit 1110 may use RF communication or Bluetooth communication. Preferably, the wireless communication unit 1110 may transmit the detection signal according to the defecation state of the wearable object 10 not only in a short distance but also in a long distance using an RF communication method. That is, it is possible to comprehensively monitor defecation states of a plurality of protected persons in real time within a building consisting of multiple floors, such as nursing homes or hospitals.

The processing unit 110 may further include an output unit 1130 that displays the defecation state according to the detection signal detected by the detection unit 130. The output unit 1130 may be provided in the form of a light-emitting diode (LED) configured to visually display data.

The processing unit 110 may further include a button unit (not illustrated) for communicating for new or modified registration of the smart defecation detection device 100. When the smart defecation detection device 100 is registered in a control server 300, which will be described below, a registration process may be activated by pressing the button unit.

As another example, the output unit 1130 may be configured as a sound output unit that audibly displays data.

Further, the smart defecation detection device 100 may be provided to adjust the sensitivity of detecting electrical signals according to the amount of defecation. Specifically, when an electrical signal value detected in real time is greater than a set value, the smart defecation detection device 100 may determine that electrical characteristics have changed, and adjust the sensitivity by adjusting the set value.

Accordingly, when the amount of defecation is small, it may not be determined that the defecation event has occurred, or as necessary, even when the amount of defecation is small, it may be determined that the defecation event has occurred.

As another example, the smart defecation detection device 100 may set a plurality of setting values and compare the electrical signal value detected in real time with the plurality of set values, and thus may obtain information on the amount of defecation.

Figure 5:
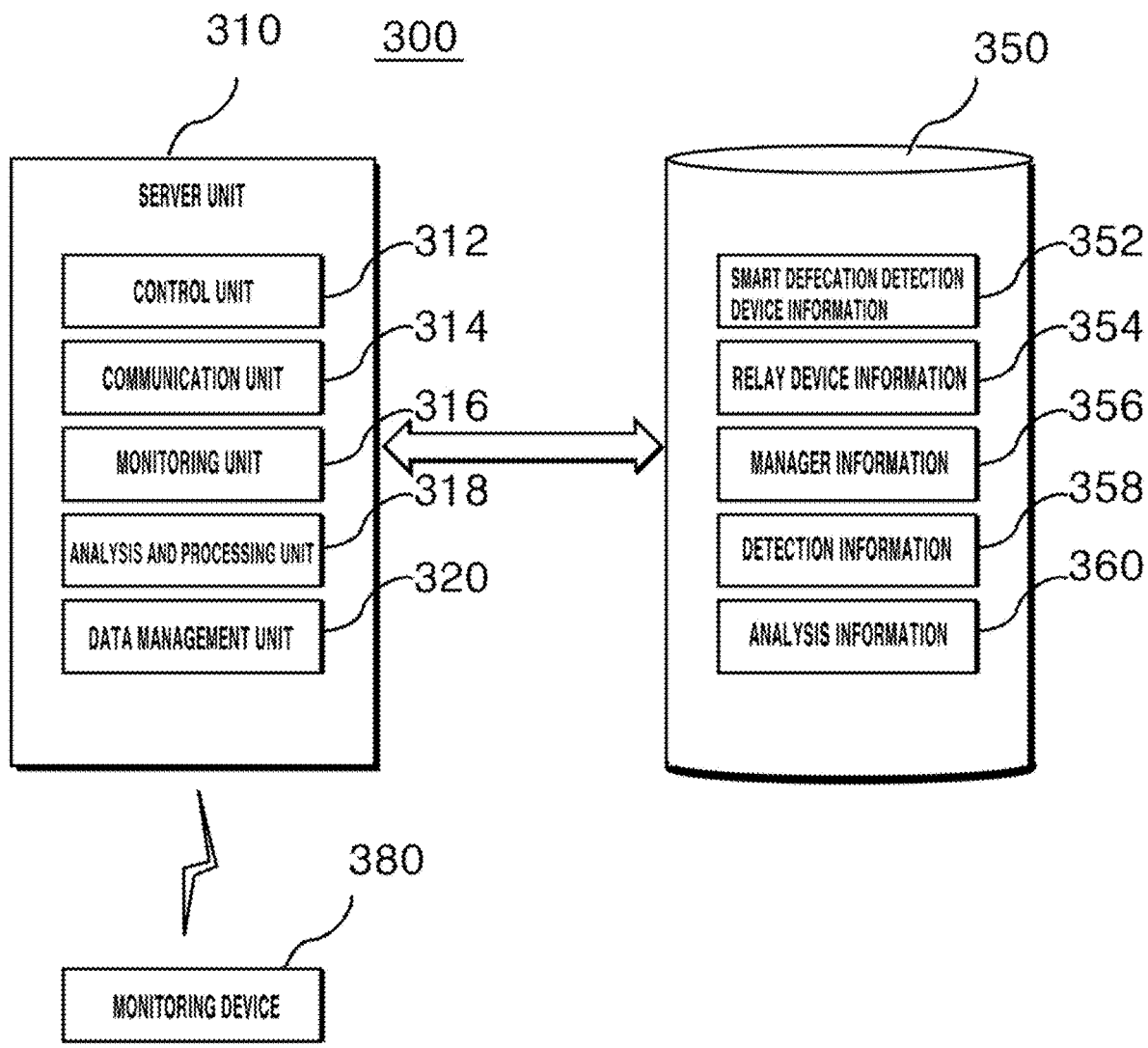
FIG. 5 is a block diagram illustrating a configuration of a control server illustrated in FIG. 3.

FIG. 5 is a block diagram illustrating a configuration of the control server illustrated in FIG. 3.

Referring to FIG. 5, the control server 300 may include a server unit 310 and a database unit 350. The control server 300 may be connected to the monitoring device 380 through a communication network.

The server unit 310 may be configured, for example, as a web server, an app server, or an application server that integrates a hardware or software platform for data analysis implemented based on artificial intelligence.

The database unit 350 may store and manage various pieces of information according to the process for processing of the control server 300 processed by the server unit 310. In this case, the database unit 350 is included in the control server 300, but as another example, the database unit 350 may be provided as an independent database server.

For example, the monitoring device 380 may be provided as a display device. The monitoring device 380 may display detection information and processing status in conjunction with the server unit 310 to monitor the detection information and the processing status of each of the smart defecation detection devices 100 in real time.

For example, the monitoring device 380 may be a personal computer (PC). As another example, the monitoring device 380 may be an integrated control display.

Further, the monitoring device 380 and the manager terminal 400 may be defined as "reception devices." That is, the reception device is any device that receives detection information detected by the smart defecation detection devices 100 and/or information on a defecation event based on the detection information.

In this case, the reception device may further include another device that receives the detection information and/or the information on the defecation event, in addition to the monitoring device 380 and the manager terminal 400. For example, the reception device may be a terminal of a guardian registered as a guardian of the protected person.

The server unit 310 may control the overall operations of the control server 300. That is, the server unit 310 may include a control unit 312, a communication unit 314, a monitoring unit 316, an analysis and processing unit 318, a data management unit 320, a smart defecation detection device management unit 322, and an event occurrence processing unit 324.

The control unit 312 may control the overall operations of the control server 300 to be processed in conjunction with the relay device 200 and the manager terminal 400. The communication unit 314 may be connected to each of the relay device 200 and the manager terminal 400 to enable communication with each other, or may be connected to at least one monitoring device 380 to enable communication with each other.

The smart defecation detection device management unit 322 may register and manage information of each of the smart defecation detection devices 100, for example, identification information of each smart defecation detection device 100, protected person information corresponding to each smart defecation detection device 100, manager information, etc.

The monitoring unit 316 may process the detection information of each of the smart defecation detection devices 100 transmitted through the relay device 200 to be monitored in real time. The analysis and processing unit 318 may collect the detection information of each of the smart defecation detection devices 100 to build bigdata, analyze a current defecation state and defecation-related habit information for each protected person, and analyze and repeatedly learn the detection information to predict a defecation pattern for each protected person.

The data management unit 320 may classify, store, and manage data of each of the smart defecation detection devices 100 using the detection information, the analysis information, and the prediction information. For example, the data management unit 320 may store and manage the detection information, the analysis information, and the prediction information by performing statistical analysis on defecation event occurrence status, notification occurrence status, defecation event processing completion status, etc. by protected person, smart defecation detection device, day/month/year, etc.

When a defecation event occurs, the event occurrence processing unit 324 may process notification information to be transmitted to the monitoring device 380 or the manager terminal 400. Further, when defecation event processing completion information is received from the manager terminal 400, the event occurrence processing unit 324 may process the corresponding information to be managed.

The database unit 350 may be controlled by the control unit 312 to store and manage at least smart defecation detection device information 352, relay device information 354, manager information 356, detection information 358, analysis information 360, prediction information 362, and recommendation information 364.

The recommendation information 364 may be recommendation information on the optimal number of baths and/or optimal bathing time for each protected person, which is extracted based on the detection information 358 and the prediction information 362.

Figure 6:
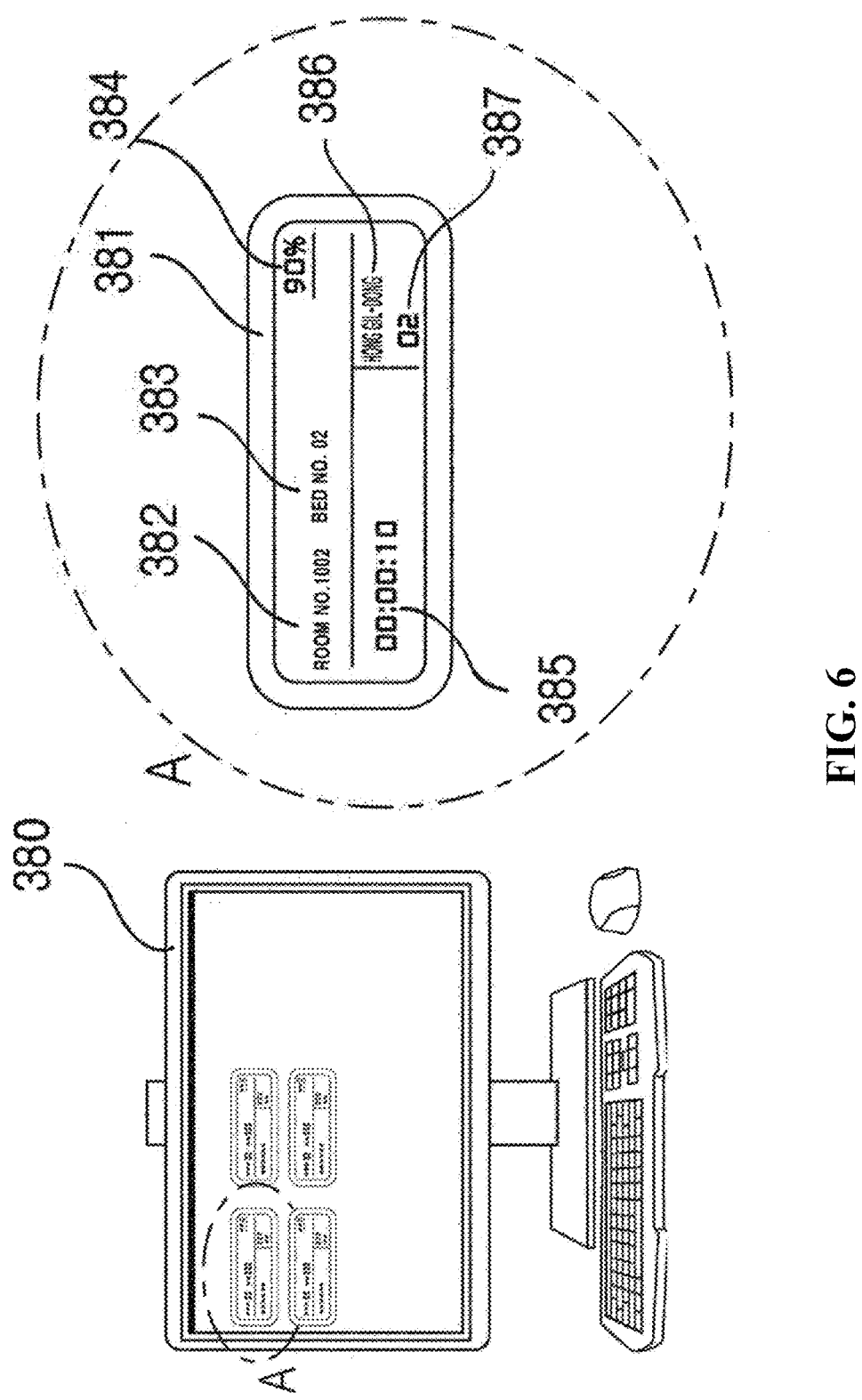
FIG. 6 is a diagram illustrating a monitoring device according to an embodiment of the present invention.

FIG. 6 is a diagram illustrating a monitoring device according to an embodiment of the present invention.

Referring to FIG. 6, the monitoring device 380 may display pre-registered detection information of the smart defecation detection device 100 in real time and may pop up notification information when an event occurs.

The monitoring device 380 may display monitoring information A corresponding to each smart defecation detection device 100. The monitoring information A may include state identification information 381, protected person information 382, 383, and 386, battery information 384, defecation event occurrence time information 385, and manager information 387.

The state identification information 381 may be shape information indicated to identify a current state of the corresponding smart defecation detection device 100 at a glance. For example, the state identification information 381 may be color information.

Specifically, the color information may include a first color indicating that communication is not smooth within a set period of time, a second color indicating that a defecation event (defecation sensing event) occurs, and a third color indicating that defecation event processing has not been completed even when a set period has elapsed from a time of occurrence of a defecation event. The state identification information 381 may be displayed in a color corresponding to the current state of the corresponding smart defecation detection device 100 among the first color, the second color, and the third color.

The protected person information 382, 383, and 386 may include a room number 382 of the protected person, a bed number 383, and a name 386 of the protected person. In addition, the protected person information 382, 383, and 386 may further include a disease name, age, sex, etc. of the protected person.

The battery information 384 may be information on a battery of the corresponding smart defecation detection device 100. For example, the battery information 384 may be information on battery remaining percentage.

For example, the defecation event occurrence time information 385 may be information on a defecation event occurrence time or information on a time elapsed from the defecation event occurrence. As another example, the defecation event occurrence time information 385 may be information on remaining time until a defecation event occurrence processing request time.

The defecation event occurrence processing request time may be different for each protected person, based on the defecation-related habit information for each protected person.

Further, the notification information may be deleted from the monitoring information A when a defecation event processing completion signal is received from the manager or the smart defecation detection device 100.

Figure 7:
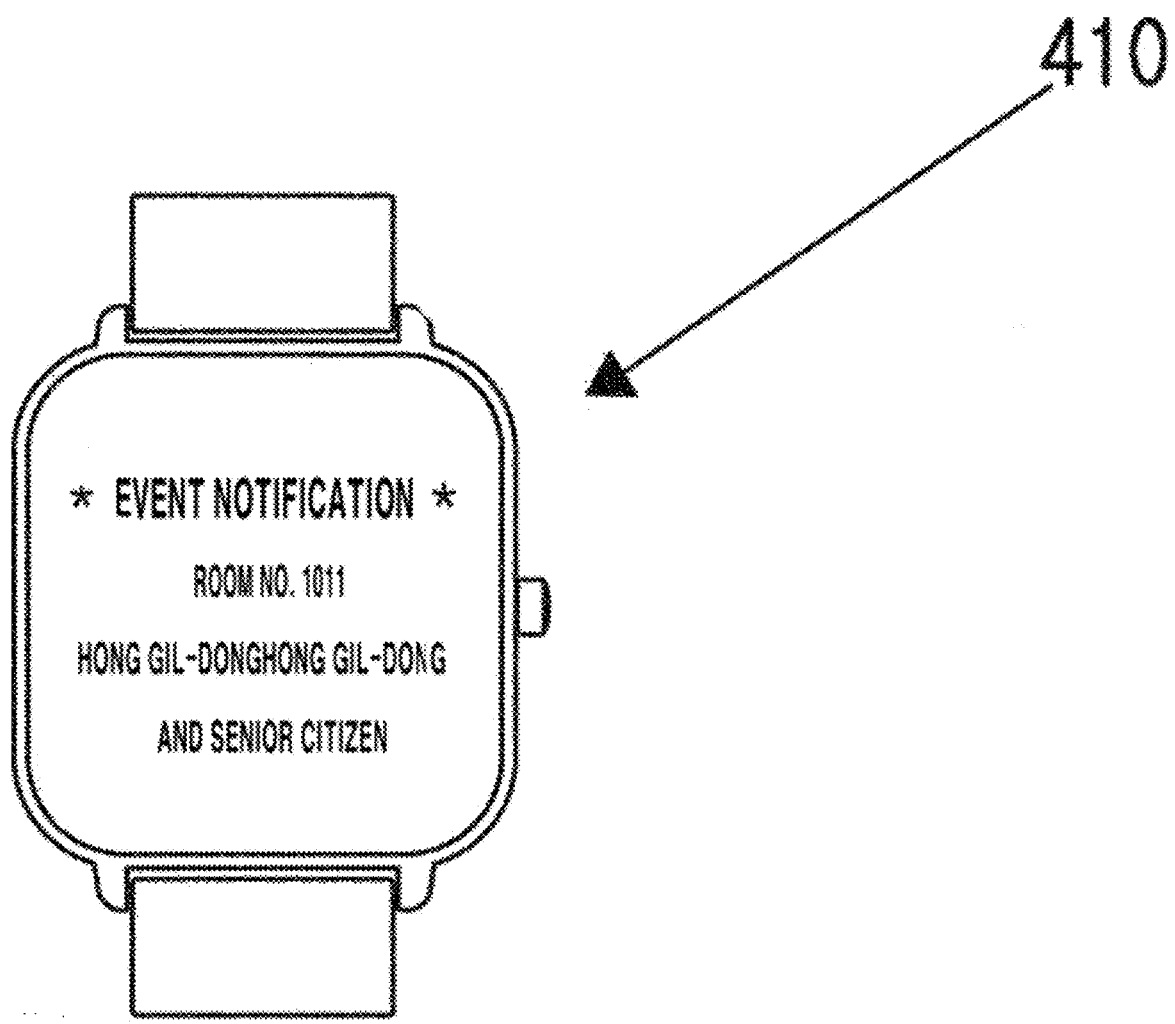
FIG. 7 is a diagram illustrating a manager terminal according to an embodiment of the present invention.

FIG. 7 is a diagram illustrating a manager terminal according to an embodiment of the present invention.

The manager terminal 400 may be a communication-capable electronic device provided to a manager in charge of a plurality of smart defecation detection devices 100. For example, the manager terminal 400 may be a smartphone, a tablet phone, a smart watch, a dedicated terminal for managing the smart defecation detection device 100, a smart ring, etc.

The manager terminal 400 may be connected to the relay device 200 or the control server 300 through a communication network, and receive and monitor detection information of each smart defecation detection device 100 in real time. Further, when a defecation event occurs or a defecation event is predicted, the notification information may be received from the relay device 200 or the control server 300, and the defecation event processing of the corresponding smart defecation detection device 100 may be performed using the received notification information.

Further, after the defecation event processing is performed, the manager terminal 400 may transmit defecation event processing completion information to the relay device 200 or the control server 300.

Further, when a diaper of the protected person in whom a defecation event has occurred is replaced, the manager may transmit defecation abnormality information of the protected person to the control server 300 through the manager terminal 400. For example, the defecation abnormality information may include an unusual defecation state of the protected person, such as diarrhea, bloody stool, bedsores, etc.

Referring to FIG. 7, in one embodiment of the present invention, it can be understood that the manager terminal 400 is provided as a smart watch 410 or a dedicated terminal 410 for managing the smart defecation detection device 100.

When detection information and notification information of the smart defecation detection device 100 in which a defecation event has occurred are received from the relay device 200 or the control server 300, the smart watch 410 or the dedicated terminal 410 may output a notification on a display.

The output notification may be at least one of an alarm notification, a text notification, and a voice notification.

The text notification may include at least one piece of information among whether a defecation event has occurred, information on the protected person in whom the defecation event has occurred, a time when the defecation event has occurred, and a time elapsed from the time at which the defecation event has occurred.

For example, as illustrated in FIG. 7, a text notification such as "Event Notification, Room No. 1011, and senior citizen Hong Gil-dong" may be output.

Figure 8:
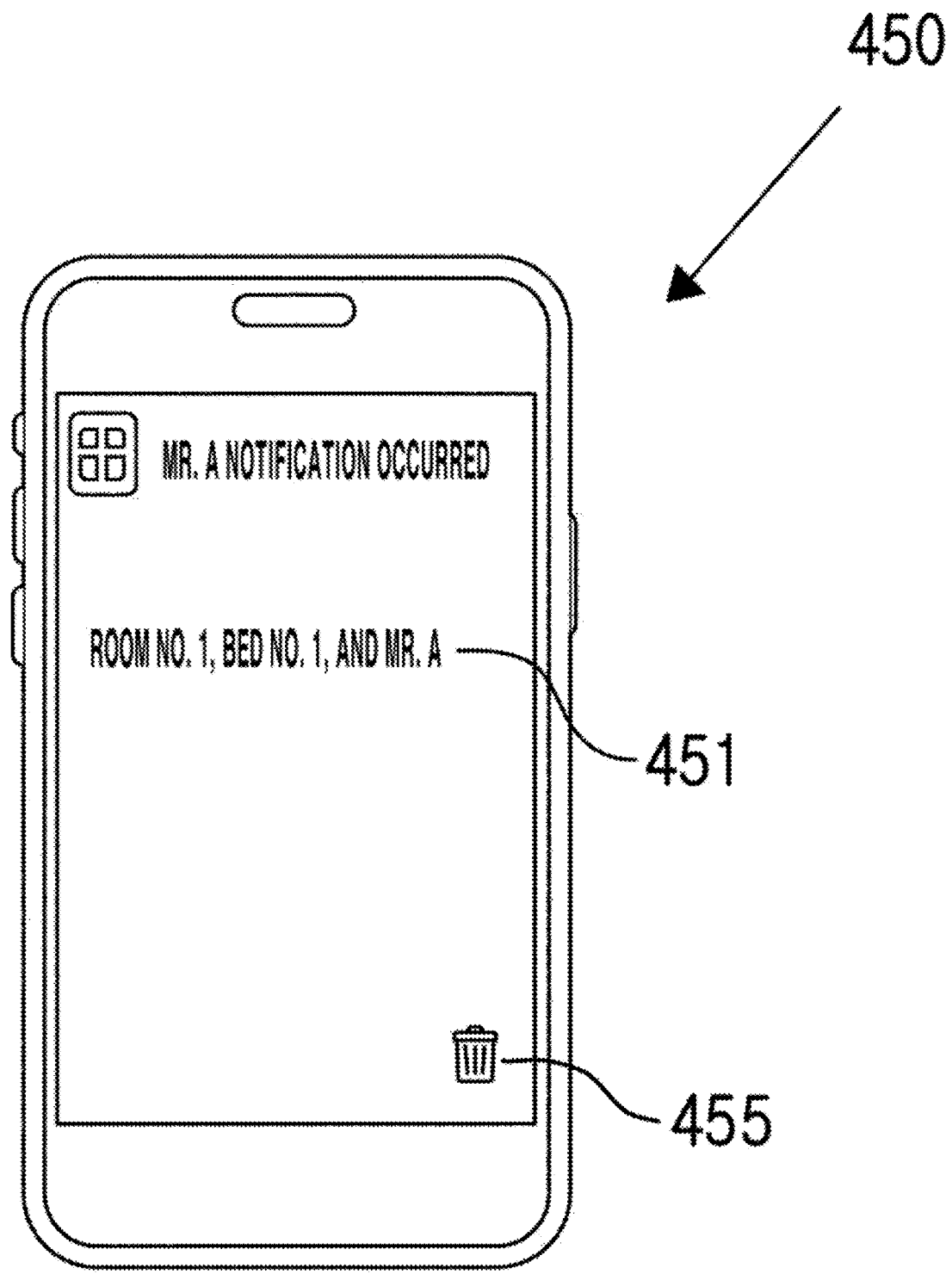
FIG. 8 is a diagram illustrating a manager terminal according to another embodiment of the present invention.

FIG. 8 is a diagram illustrating a manager terminal according to another embodiment of the present invention.

Referring to FIG. 8, the manager terminal 400 may be a smartphone 450.

When detection information and notification information of the smart defecation detection device 100 in which a defecation event has occurred are received from the relay device 200 or the control server 300, the smartphone 450 may output a notification on a display.

The output notification may be at least one of an alarm notification, a text notification, and a voice notification.

The text notification may include at least one piece of information among whether a defecation event has occurred, information on the protected person in whom the defecation event has occurred, a time when the defecation event has occurred, and a time elapsed from the time at which the defecation event has occurred.

For example, as illustrated in FIG. 8, a text notification such as "Room No. 1, Bed No. 1, and Mr. A" may be output.

Further, the smartphone 450 may output a defecation event processing completion button 455 on the display. After defecation event processing is completed, the manager may press the defecation event processing completion button 455 and transmit a defecation event processing completion signal to the relay device 200 or the control server 300.

For example, the defecation event processing completion signal may be a notification deletion signal.

Figure 9:
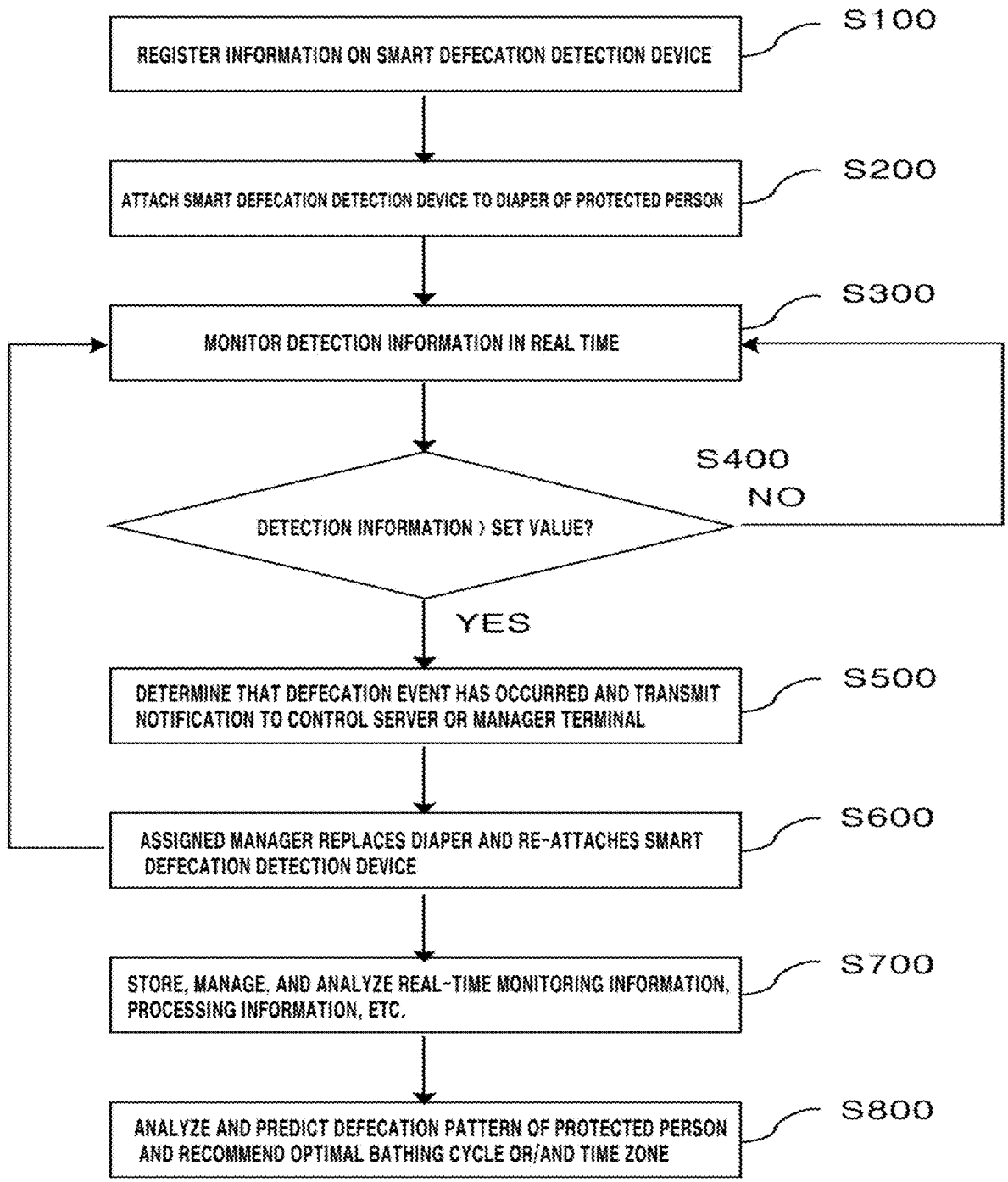
FIG. 9 is a flowchart illustrating a processing procedure of the healthcare system including the smart defecation detection device according to the present invention.

FIG. 9 is a flowchart illustrating a processing procedure of the healthcare system including the smart defecation detection device according to the present invention.

Referring to FIG. 9, in operation S100, the healthcare system 1 of the present invention registers information on a smart defecation detection device 100. In this case, the information on the smart defecation detection device 100 may include ID information of the smart defecation detection device 100, protected person information, and manager information.

The protected person information may be a hospital room and bed number of the protected person, and name information of the protected person. The manager information may be manager code information or manager name information of a manager assigned to manage each protected person.

In operation S200, the manager may attach the registered smart defecation detection device 100 to an assigned wearable object 10 of the protected person, that is, a diaper.

In operation S300, the smart defecation detection device 100 may transmit detection information to the relay device 200 in real time. The relay device 200 may transmit the transmitted detection information to the control server 300 or the manager terminal 400 in real time. The manager may monitor the detection information of each smart defecation detection device 100 in real time through the monitoring device 380 of the control server 300 or the manager terminal 400.

In operation S400, whether the detection information is greater than a set value may be determined in real time. The set value may be a reference value for determining that a defecation event has occurred based on the detection information.

In this case, the set value may be adjusted by the manager to detect the sensitivity for detecting defecation.

Further, the set value is set as a plurality of values, so that information on the amount of defecation may be determined.

In operation S500, when it is determined that the detection information is greater than the set value, it is determined that a defecation event has occurred, and notification information may be transmitted to the monitoring device 380 of the control server 300 or the manager terminal 400. In this case, the manager terminal 400 that receives the notification information may be a manager terminal 400 of a manager corresponding to the manager information registered in the corresponding smart defecation detection device 100.

Additionally, when defecation event processing completion information is not detected within a set period of time after notification of the occurrence of the defecation event is performed, the relay device 200 or the control server 300 may additionally transmit the notification information.

As another example, when the defecation event processing completion information is not detected within a set period of time after notification of the occurrence of the defecation event is performed, the relay device 200 or the control server 300 may transmit a notification to a manager terminal 400 of a deputy manager registered in the corresponding smart defecation detection device 100.

In operation S600, the manager (or assigned manager) corresponding to the manager information registered in the smart defecation detection device 100 may replace the wearable object 10 in which a defecation event has occurred, that is, a diaper, with a new diaper, and re-attach the smart defecation detection device 100 to the replaced diaper.

In this case, the smart defecation detection device 100 may transmit detection information detected in the replaced diaper in real time, and the control server 300 may obtain defecation event processing completion information using the detection information.

In operation S700, the control server 300 may store, manage, and analyze real-time monitoring information (detection information and defecation event occurrence information), processing information, etc.

In operation S800, the control server 300 may analyze a current defecation state and defecation-related habit information for each protected person based on the detection information and the processing information, and predict a defecation pattern for each protected person.

Further, the control server 300 may analyze and recommend an optimal bathing cycle or/and an optimal bathing time for each protected person based on the detection information, analysis information, and prediction information.

Although embodiments of the present invention have been described in more detail with reference to the accompanying drawings, the present invention is not necessarily limited to these embodiments, and various modifications may be made without departing from the technical spirit of the present invention. Therefore, the embodiments disclosed in the present invention should be considered in a descriptive sense only and not for purposes of limitation. Accordingly, the scope of the present invention is not limited by these embodiments. Therefore, the above-described embodiments should be considered in a descriptive sense only and not for purposes of limitation. The spirit and scope of the present invention should be interpreted by the appended claims and encompass all equivalents falling within the scope of the appended claims.

Therefore, other implementations, other embodiments and equivalents within the scope of the appended claims are included in the range of the claims to be described.

The invention claimed is:

1. A healthcare system including a smart defecation detection device, comprising:
   a smart defecation detection device that is detachable to a wearable object of a protected person and detects defecation of the protected person, wherein the smart defecation detection device is provided as one of a plurality of smart defecation detection devices;
   a relay device that is communicatively connected to the smart defecation detection devices through a first communication network and receives detection information in real time from the plurality of smart defecation detection devices;
   a control server that is communicatively connected to the relay device through a second communication network, receives the detection information of the plurality of smart defecation detection devices in real time from the relay device, and comprehensively manages whether a defecation event has occurred and whether processing of the defecation event has been completed for each protected person, based on the detection information; and
   a reception device configured to receive notification information so that an assigned manager or ward/management station in charge of the protected person in whom the defecation event has occurred is allowed to be aware of the defecation event when it is determined that the defecation event has occurred based on the detection information of the smart defecation detection device,
   wherein information on the protected person matching each smart defecation detection device and information on the assigned manager in charge of the protected person are registered in the control server,
   the notification information includes information on the protected person in whom the defecation event has occurred and information on a time of occurrence of the defecation event,
   the reception device includes a monitoring device that is connected to the control server, is provided as a display device, and displays the detection information and processing status of the plurality of smart defecation detection devices, and a manager terminal that is provided to the assigned manager in charge of the plurality of smart defecation detection devices and receives the detection information of the smart defecation detection devices and the notification information when the defecation event occurs,
   the manager terminal is communicatively connected to the relay device through a third communication network and communicatively connected to the control server through a fourth communication network,
   after the processing of the defecation event is completed, the assigned manager transmits information on the completion of the defecation event processing and defecation abnormality information of the protected person in whom the defecation event has occurred to the control server through the manager terminal,
   the defecation abnormality information includes an unusual defecation state of the protected person, and the unusual defecation state of the protected person includes diarrhea, bedsores, or bloody stool,
   the information on the assigned manager includes manager code information,
   the control server matches the assigned manager in charge of the smart defecation detection device to a manager working in real time, based on commuting information of the manager and the manager code information matching each manager each time he or she goes to work, and
   the notification information when the defecation event occurs is transmitted to the manager terminal of the manager working in real time, who is matched to the assigned manager in charge of the smart defecation detection device where the defecation event has occurred, based on the manager code information matched to the smart defecation detection device where the defecation event has occurred.

2. The healthcare system of claim 1, wherein the smart defecation detection device includes:
   a battery unit provided to be rechargeable;
   a wireless communication unit provided to wirelessly communicate with the relay device; and
   a detection unit that detects an electrical signal according to the defecation state of the wearable object, and
   the electrical signal of the detection unit is changed based on detecting of at least one of ammonia, humidity, and temperature is changed.

3. The healthcare system of claim 1, wherein the smart defecation detection device is re-attached after the assigned manager replaces the wearable object in which the defecation event has occurred with a new wearable object.

4. The healthcare system of claim 1, wherein the control server receives the detection information of each of the smart defecation detection devices in real time, processes to monitor a defecation event occurring in the smart defecation detection device and a defecation processing status, and collects and analyzes information obtained from the monitoring, and
   the control server predicts a defecation pattern for each protected person based on the collected and analyzed information and recommends an optimal bathing cycle or an optimal bathing time for each protected person based on the predicted defecation pattern for each protected person.

5. The healthcare system of claim 1, wherein the control server receives the detection information of each of the smart defecation detection devices in real time, processes to monitor a defecation event occurring in the smart defecation detection device and a defecation processing status, and analyzes a current defecation state and defecation-related habit information for each protected person based on information obtained from the monitoring,
   the defecation-related habit information includes bedsore history of the protected person, skin sensitivity information, and information on the level of psychological sensitivity of the protected person,
   the information on the time of the occurrence of the defecation event includes information on a remaining time from a time point of the occurrence of the defecation event to a processing request time, and
   the control server recommends and sets a customized processing request time when the defecation event occurs for each protected person, based on the defecation-related habit information for each protected person.

6. The healthcare system of claim 1, wherein the assigned manager includes a primary manager and a deputy manager, and when a defecation event processing completion signal is not received by the control server within a set time from a time point at which the notification information is transmitted to the assigned manager in charge of the protected person in whom the defecation event has occurred, the notification information is additionally transmitted to a manager terminal of the deputy manager.

* * * * *